(12) United States Patent
Pan et al.

(10) Patent No.: US 9,358,221 B2
(45) Date of Patent: *Jun. 7, 2016

(54) METHOD FOR MANUFACTURING COMPOSITION FOR LOWERING BLOOD LIPID AND ELEVATING HIGH-DENSITY LIPOPROTEIN (71) Applicant: SunWay Biotech Co., Ltd., Taipei (TW)

(72) Inventors: Tzu-Ming Pan, Taipei (TW); Chun-Lin Lee, Taipei (TW); Cheng-Lun Wu, Taipei (TW)

(73) Assignee: SUNWAY BIOTECH CO., LTD., Taipei (TW)

( * ) Notice: Subject to any disclaimer, the term of this patent is extended or adjusted under 35 U.S.C. 154(b) by 6 days.

This patent is subject to a terminal disclaimer.

(21) Appl. No.: 13/788,674

(22) Filed: Mar. 7, 2013

(65) Prior Publication Data
US 2013/0184473 A1    Jul. 18, 2013

Related U.S. Application Data (62) Division of application No. 13/215,414, filed on Aug. 23, 2011, now abandoned.

(60) Provisional application No. 61/505,496, filed on Jul. 7, 2011.

(51) Int. Cl.
C07D 307/00    (2006.01)
A61K 31/365    (2006.01)
C07D 493/04    (2006.01)
A61K 31/353    (2006.01)

(52) U.S. Cl.
CPC .............. A61K 31/365 (2013.01); A61K 31/353 (2013.01); C07D 493/04 (2013.01)

(58) Field of Classification Search
CPC ........................... A61K 31/365; C07D 493/04
USPC ....................................................... 424/195.16
See application file for complete search history.

(56) References Cited

PUBLICATIONS

Lee et al. Applied Microbial and Cell Physiology, 2006, 72, 1254-1262.*
USPTO Restriction Requirement for Parent Application (U.S. Appl. No. 13/215,414) mailed on Nov. 5, 2012.
USPTO Office Action for Parent Application (U.S. Appl. No. 13/215,414) mailed on Jan. 22, 2013.
Lee et al. J. Agric. Food Chem. 2010, 58, 9013-9019.
Lin et al. J. Sci. Food Agric. 2011, 91, 1751-1758.
Lee et al. Appl. Microbiol Biotechnol (2006) 72: 1254-1262.

* cited by examiner

Primary Examiner — Nizal Chandrakumar
(74) Attorney, Agent, or Firm — Anova Law Group, PLLC (57) ABSTRACT The present invention discloses a composition for lowering blood lipid and elevating high-density lipoprotein and a method for manufacturing the same; the composition comprises monascin or ankaflavin, or a combination thereof; the manufacturing method comprises the steps of: treating a Monascus fermented product with acetone for three times; elevating the concentration of the Monascus fermented product by a process of decompress concentration; and extracting the monascin and the ankaflavin from the Monascus fermented product with a silica gel column chromatography, a Sephadex LH-20 column chromatography, the silica gel column chromatography, and a preparative high performance liquid chromatography sequentially.

2 Claims, 12 Drawing Sheets

METHOD FOR MANUFACTURING COMPOSITION FOR LOWERING BLOOD LIPID AND ELEVATING HIGH-DENSITY LIPOPROTEIN

BACKGROUND OF THE INVENTION

1. Field of the Invention

The present invention relates to composition for lowering blood lipid and elevating high-density lipoprotein, and more particularly to a composition containing monascin or ankaflavin, or a combination thereof, for lowering blood lipid and elevating high-density lipoprotein.

2. Description of the Prior Art

The content of cholesterol in blood is closely related to the incidence of cardiovascular diseases. According to previous studies, dyslipidemia plays an important role in the cardiovascular diseases, thus the concentration of cholesterol in blood can be a well predictor for the cardiovascular diseases. When the concentration of serum cholesterol is more than 200 mg/dL, the probability of dying of coronary heart disease is raised rapidly. A person who has high content of cholesterol should have high morbidity rate of coronary heart disease and high death rate, but if the content of cholesterol is lowered by the treatment of a medical or a non-medical process, the incidence rate of the cardiovascular diseases caused by coronary sclerosis can be decreased significantly.

In recent years, health foods are developed vigorously, and multi-functional *Monascus* fermented products are gradually paid attention. In Asia, the application of *Monascus* species in food and medicine has thousand years of history.

The important secondary metabolites of *Monascus* species include: (1) a group of pigments, including red pigments (rubropunctamine and monascorubramine), yellow pigments (ankaflavin and monascin) and orange pigments (rubropunctanin and monascorubrin); (2) cholesterol-lowering substance, such as monacolin K (also called as lovastatin, mevinolin and mevacor); (3) blood pressure lowering substance, such as γ-aminobutyric acid (GABA); and (4) antioxidants, including dimerumic acid and 3-hydoxy-4-methoxy-benzoic acid.

In the above important secondary metabolites of *Monascus* species, owing to the monacolin K can reduce the activity of hydroxyl methylglutaryl-CoA reductase (HMG-CoA reductase), which is a key enzyme in the process of cholesterol biosynthesis, the monacolin K has a significantly effect for lowering cholesterol.

On the other hand, cholesterol in blood can be divided into two categories according to their density, including High Density Lipoprotein-Cholesterol (HDL-C) and Low Density Lipoprotein-Cholesterol (LDL-C). Many researches indicate that HDL-C is a kind of good cholesterol, and LDL-C is bad cholesterol. High concentration of HDL-C and low concentration of LDL-C are helpful in decreasing the incidence of cardiovascular disease and atherosclerosis.

Owing to total cholesterol (TC) is composed of HDL-C, LDL-C, triglyceride (TG), and other lipoprotein cholesterols, the amount of HDL-C and LDL-C can be substantially increased in company with the elevation of the concentration of TC. Most researches illustrate that after the concentration of TC being lowered by cholesterol-lowering drugs, the concentration of HDL-C is also decreased greatly. However, if the concentration of HDL-C can be maintained or elevated, the prevention of cardiovascular diseases can be achieved.

However, although the above-mentioned monacolin K has the effect of lowering cholesterol, the concentration of HDL-C can not be elevated by monacolin K, and the effect of preventing cardiovascular diseases and atherosclerosis by monacolin K is very limited.

In view of this, it is necessary to provide a novel composition and a method for manufacturing the same, wherein the composition has effects of lowering blood lipid and elevating the concentration of HDL-C simultaneously, so as to decrease the incidence of cardiovascular diseases and atherosclerosis effectively.

SUMMARY OF THE INVENTION

In view of the above shortcomings of the prior art, the inventors of the present invention resorted to past experience, imagination, and creativity, performed experiments and researches repeatedly, and eventually devised the present invention, a composition for lowering blood lipid and elevating high-density lipoprotein and a method for manufacturing the same.

The major objective of the present invention is to provide the composition for lowering blood lipid and elevating high-density lipoprotein, which comprises monascin and can lower the concentration of blood lipid and elevate the concentration of high-density lipoprotein effectively.

According to the above objective, the present invention provides a composition for lowering blood lipid and elevating high-density lipoprotein, wherein the composition comprises monascin, which is a *Monascus* yellow pigment and extracted from a *Monascus* fermented product.

Another objective of the present invention is to provide the method for manufacturing a composition for lowering blood lipid and elevating high-density lipoprotein, by a series of extraction processes, a composition containing monascin can be obtained, and the composition can lower the concentration of blood lipid and elevate the concentration of high-density lipoprotein effectively.

According to the above objective, the present invention provides a method for manufacturing a composition for lowering blood lipid and elevating high-density lipoprotein, wherein the method comprises the steps of: (1) providing a *Monascus* fermented product; (2) treating the *Monascus* fermented product with acetone for three times; (3) elevating the concentration of the product obtained from the previous step by a process of decompress concentration in a specific temperature range; (4) separating a pigment fraction from the product obtained from the prevwus step by a silica gel column chromatography; (5) separating a yellow pigment fraction from the pigment fraction by a Sephadex LH-20 column chromatography; (6) separating a fraction containing monascin and ankaflavin from the yellow pigment fraction by the silica gel column chromatography; and (7) separating monascin from the fraction containing monascin and ankaflavin obtained from the previous step by a preparative high performance liquid chromatography (pre-HPLC). "Decompress concentration," as used in the present disclosure, refers to a process to increase the concentration of a solute in a solution by reducing the air pressure over the solution below the ambient air pressure. The reduced air pressure may be determined empirically.

Further objective of the present invention is to provide the composition for lowering blood lipid and elevating high-density lipoprotein, which comprises ankaflavin and can lower the concentration of blood lipid and elevate the concentration of high-density lipoprotein effectively.

According to the above objective, the present invention provides a composition for lowering blood lipid and elevating high-density lipoprotein, wherein the composition comprises ankaflavin, which is a *Monascus* yellow pigment and extracted from a *Monascus* fermented product.

Further objective of the present invention is to provide the method for manufacturing a composition for lowering blood lipid and elevating high-density lipoprotein, by a series of extraction processes, a composition containing ankaflavin can be obtained, and the composition can lower the concentration of blood lipid and elevate the concentration of high-density lipoprotein effectively.

According to the above objective, the present invention provides a method for manufacturing a composition for lowering blood lipid and elevating high-density lipoprotein, wherein the method comprises the steps of: (1) providing a *Monascus* fermented product; (2) treating the *Monascus* fermented product with acetone for three times; (3) elevating the concentration of the product obtained from the previous step by a process of decompress concentration in a specific temperature range; (4) separating a pigment fraction from the product obtained from the previous step by a silica gel column chromatography; (5) separating a yellow pigment fraction from the pigment fraction by a Sephadex LH-20 column chromatography; (6) separating a fraction containing monascin and ankaflavin from the yellow pigment fraction by the silica gel column chromatography; and (7) separating ankaflavin from the fraction containing monascin and ankaflavin obtained from the previous step by a pre-HPLC.

Further objective of the present invention is to provide the composition for lowering blood lipid and elevating high-density lipoprotein, which comprises monascin and ankaflavin and can lower the concentration of blood lipid and elevate the concentration of high-density lipoprotein effectively.

According to the above objective, the present invention provides a composition for lowering blood lipid and elevating high-density lipoprotein, wherein the composition comprises monascin and ankaflavin, which are both *Monascus* yellow pigments and extracted from a *Monascus* fermented product.

Further objective of the present invention is to provide the method for manufacturing a composition for lowering blood lipid and elevating high-density lipoprotein, by a series of extraction processes, a composition containing monascin and ankaflavin can be obtained, and the composition can lower the concentration of blood lipid and elevate the concentration of high-density lipoprotein effectively.

According to the above objective, the present invention provides a method for manufacturing a composition for lowering blood lipid and elevating high-density lipoprotein, wherein the method comprises the steps of: (1) providing a *Monascus* fermented product; (2) treating the *Monascus* fermented product with acetone for three times; (3) elevating the concentration of the product obtained from the previous step by a process of decompress concentration in a specific temperature range; (4) separating a pigment fraction from the product obtained from the previous step by a silica gel column chromatography; (5) separating a yellow pigment fraction from the pigment fraction by a Sephadex LH-20 column chromatography; (6) separating a fraction containing monascin and ankaflavin from the yellow pigment fraction by the silica gel column chromatography; (7) separating monascin and ankaflavin respectively from the fraction containing monascin and ankaflavin obtained from the previous step by a pre-HPLC; and (8) mixing the monascin and the ankaflavin according to a specific ratio.

BRIEF DESCRIPTION OF THE DRAWINGS

For a complete understanding of the aspects, structures and techniques of the invention, reference should be made to the following detailed description and accompanying drawings wherein.

DETAILED DESCRIPTION OF THE PREFERRED EMBODIMENTS

To achieve the foregoing objectives and effects, the inventors utilize a *Monascus* fermented product as an extraction substrate, and extract the *Monascus* fermented product by a series of specific processes, under constant tests and regulations, thus achieving a composition for lowering blood lipid and elevating high-density lipoprotein and a method for manufacturing the same of the present invention. Hereinafter, the composition for lowering blood lipid and elevating high-density lipoprotein and the method for manufacturing the same according to a first, a second and a third preferred embodiment of the present invention are described in detail to illustrate the ingredients of the composition and the method for manufacturing the same of the present invention.

Figure 1:
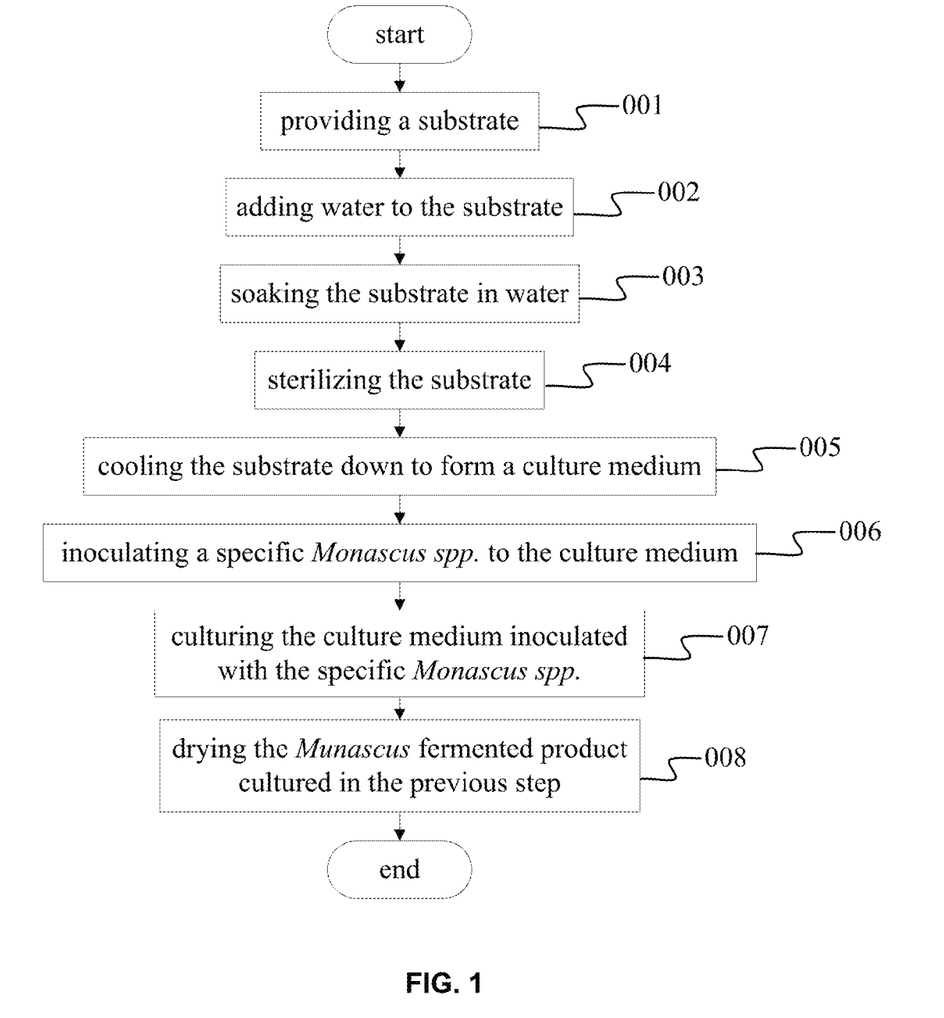
FIG. 1 is a flow chart diagram of a method for manufacturing a *Monascus* fermented product of the present invention.

Before introducing the preferred embodiments of the present invention, the manufacturing method of a *Monascus* fermented product should be illustrated first. Referring to FIG. 1, which is a flow chart diagram of the method for manufacturing the *Monascus* fermented product of the present invention. The method comprises the steps of: (step 001) providing a substrate, which can be rice or dioscorea, wherein the water content of the substrate should be below 15%, and the optimal water content is 7%; (step 002) adding water to the substrate to make the ratio of the substrate to water be 1:0.5%~1:1.5%, wherein the optimal ratio is 1:0.75%; (step 003) soaking the substrate in water, wherein the soaking time is 0~60 min, and the optimal time is 30 min; (step 004) sterilizing the substrate, wherein the sterilization condition is 121° C. for 10~60 min; (step 005) cooling the substrate down to form a culture medium; (step 006) inoculating a specific *Monascus* spp. to the culture medium, wherein the specific *Monascus* spp. can be *Monascus purpureus*; (step 007) culturing the culture medium inoculated with the specific *Monascus* spp., wherein the culture medium is cultured under a temperature of 25~37° C., a humidity of 50~80%, and for 8~20 days, and the optimal culture condition is the temperature of 30, the humidity of 60%, and for 10 days; (step 008) drying the *Munascus* fermented product cultured in the previous step to make the *Munascus* fermented product have a water content below 15%, wherein the optimal water content is 6%. By the above processes, the *Monascus* fermented product is manufactured.

In the method for manufacturing the *Monascus* fermented product of the present invention, the strains of *Monascus purpureus* can be selected from *Monascus purpureus* NTU 568 or *Monascus purpureus* PAN 790.

*Monascus purpureus* NTU 568 is deposited in Agricultural Research Culture Collection (NRRL) in Nov. 13, 2009, and the given accession number is NRRL 50338. The characteristics of *Monascus purpureus* NTU 568 includes rapid growth, strong ability of starch hydrolysis, and strong ability of metabolites production. The basic culture manner of *Monascus purpureus* NTU 568 is to be cultured with a medium containing 2% of rice powder, the best culture temperature is 30° C., the best culture time is 48 hours, the best culture pressure is 1 atm, and the growth of *Monascus purpureus* NTU 568 is oxygen dependent.

*Monascus purpureus* PAN 790 is deposited in Agricultural Research Culture Collection (NRRL) in Nov. 13, 2009, and the given accession number is NRRL 50337. The characteristics of *Monascus purpureus* PAN 790 includes slow growth, being able to produce large amount of monacolin K, and being mutated in and cloned from red mold rice. The culture medium for *Monascus purpureus* PAN 790 includes 2% of rice powder; the culture temperature is 30° C.; the culture time is 48 hours; the culture pressure is 1 atm; the sterilization manner for *Monascus purpureus* PAN 790 is 121° C. for 20 min; the pH value before sterilization is 5; the growth of *Monascus purpureus* PAN 790 is oxygen dependent; and the storage temperature for *Monascus purpureus* PAN 790 is 4° C.

Subsequently, the first preferred embodiment of the present invention is described in detail. The composition for lowering blood lipid and elevating high-density lipoprotein according to the first preferred embodiment of the present invention contains monascin, which is a *Monascus* yellow pigment, and extracted from the above-mentioned *Monascus* fermented product. Wherein an amount of the monascin taken by an adult is more than 2.4 mg per day, so that the concentration of blood lipid can be lowered and the concentration of the high-density lipoprotein in blood can be elevated effectively.

Figure 2:
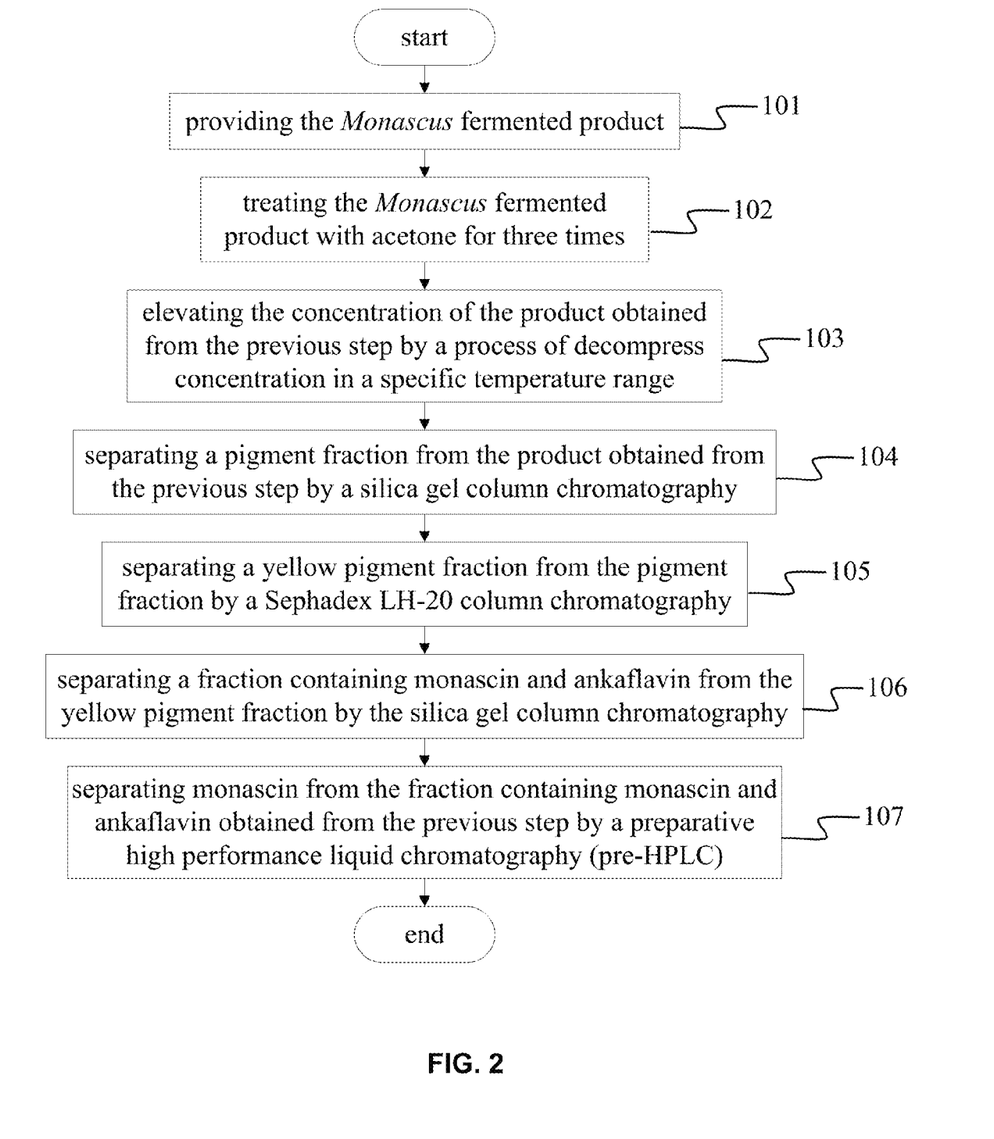
FIG. 2 is a flow chart diagram of a method for manufacturing a composition for lowering blood lipid and elevating high-density lipoprotein according to a first preferred embodiment of the present invention.

Referring to FIG. 2, which is a flow chart diagram of a method for manufacturing the composition for lowering blood lipid and elevating high-density lipoprotein according to the first preferred embodiment of the present invention. The method includes the steps of: (step 101) providing the *Monascus* fermented product; (step 102) treating the *Monascus* fermented product with acetone for three times, wherein the ratio of the *Monascus* fermented product to the acetone is 1:10~1:50; (step 103) elevating the concentration of the product obtained from the previous step by a process of decompress concentration in a specific temperature range, wherein the specific temperature range is 40~60; (step 104) separating a pigment fraction from the product obtained from the previous step by a silica gel column chromatography; (step 105) separating a yellow pigment fraction from the pigment fraction by a Sephadex LH-20 column chromatography; (step 106) separating a fraction containing monascin and ankaflavin from the yellow pigment fraction by the silica gel column chromatography; and (step 107) separating monascin from the fraction containing monascin and ankaflavin obtained from the previous step by a preparative high performance liquid chromatography (pre-HPLC).

Figure 3:
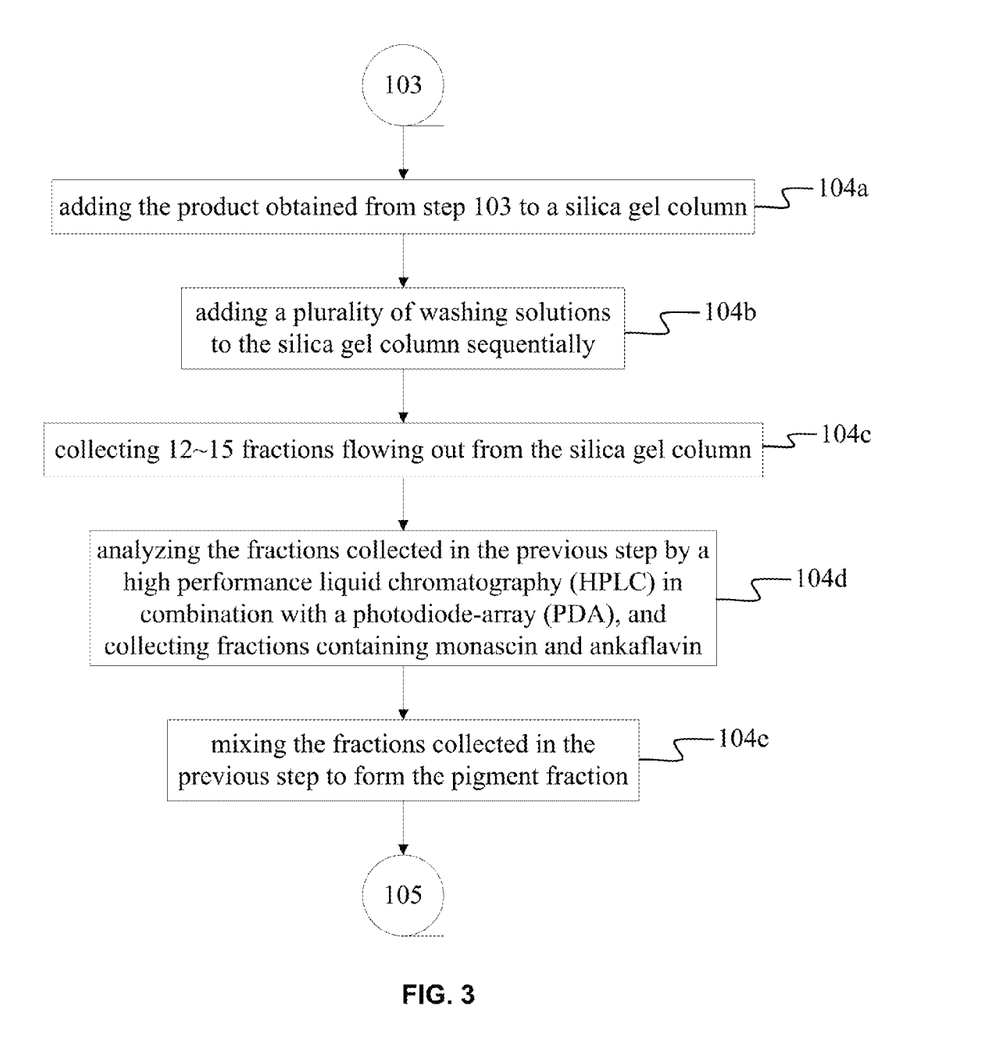
FIG. 3 is a flow chart diagram of detailed steps of step 104 according to the first preferred embodiment of the present invention.

Referring to FIG. 3, which is a flow chart diagram of detailed steps of step 104 according to the first preferred embodiment of the present invention. The above step 104 can be subdivided into the following steps of: (step 104a) adding the product obtained from step 103 to a silica gel column; (step 104b) adding a plurality of washing solutions to the silica gel column sequentially, wherein the plurality of washing solutions are Hexane, Hexane:Ethanol=9:1, Hexane:Ethanol=8:2, Hexane:Ethanol=7:3, Hexane:Ethanol=1:1, and Ethanol sequentially; (step 104c) collecting 12~15 fractions flowing out from the silica gel column, wherein the time period of each fraction flowing out from the silica gel column is 5~10 min; (step 104d) analyzing the fractions collected in the previous step by a high performance liquid chromatography (HPLC) in combination with a photodiode-array (PDA), and collecting fractions containing monascin and ankaflavin; and (step 104e) mixing the fractions collected in the previous step to form the pigment fraction.

Figure 4:
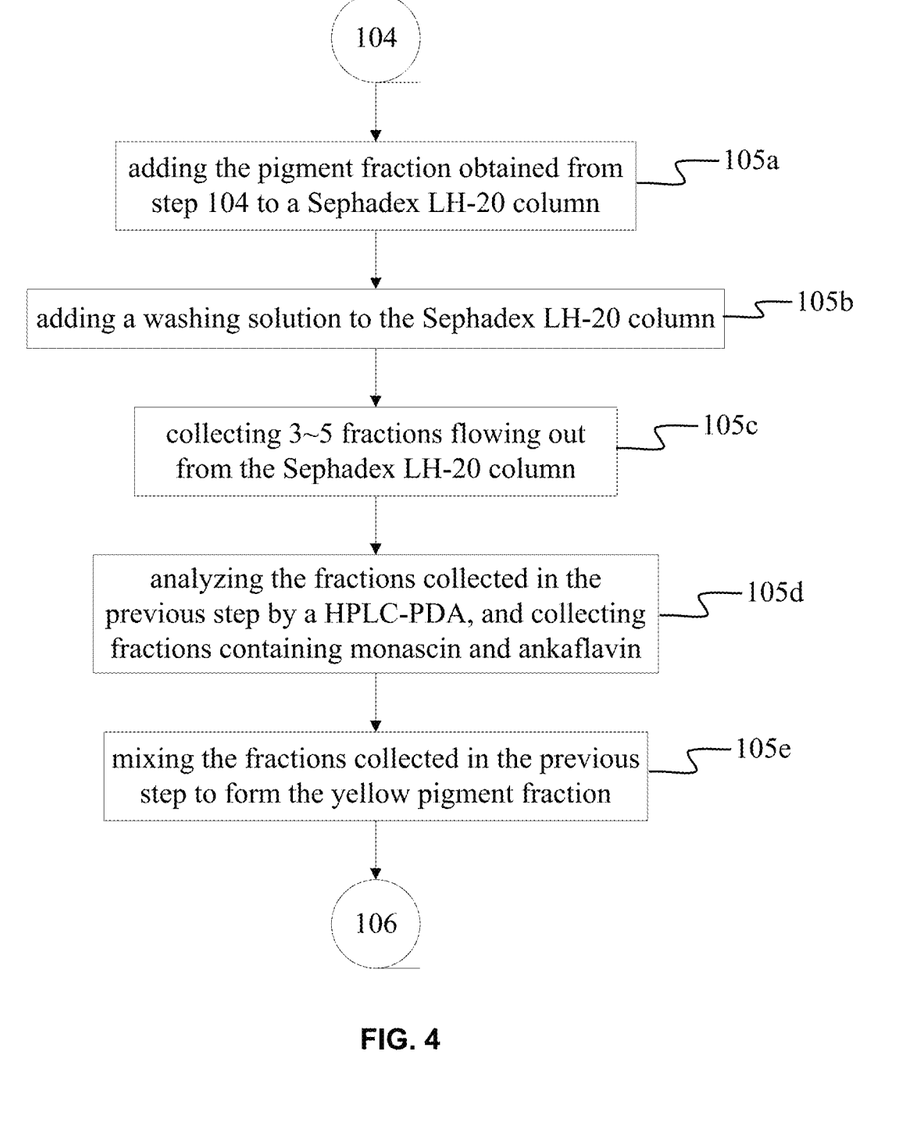
FIG. 4 is a flow chart diagram of detailed steps of step 105 according to the first preferred embodiment of the present invention.

Referring to FIG. 4, which is a flow chart diagram of detailed steps of step 105 according to the first preferred embodiment of the present invention. The above step 105 can be subdivided into the following steps of: (step 105a) adding the pigment fraction obtained from step 104 to a Sephadex LH-20 column; (step 105b) adding a washing solution to the Sephadex LH-20 column, wherein the washing solution is Methanol:Acetonitrile=9:1; (step 105c) collecting 3~5 fractions flowing out from the Sephadex LH-20 column, wherein the time period of each fraction flowing out from the silica gel column is 5~10 min; (step 105d) analyzing the fractions collected in the previous step by a HPLC-PDA, and collecting fractions containing monascin and ankaflavin; and (step 105e) mixing the fractions collected in the previous step to form the yellow pigment fraction.

Figure 5:
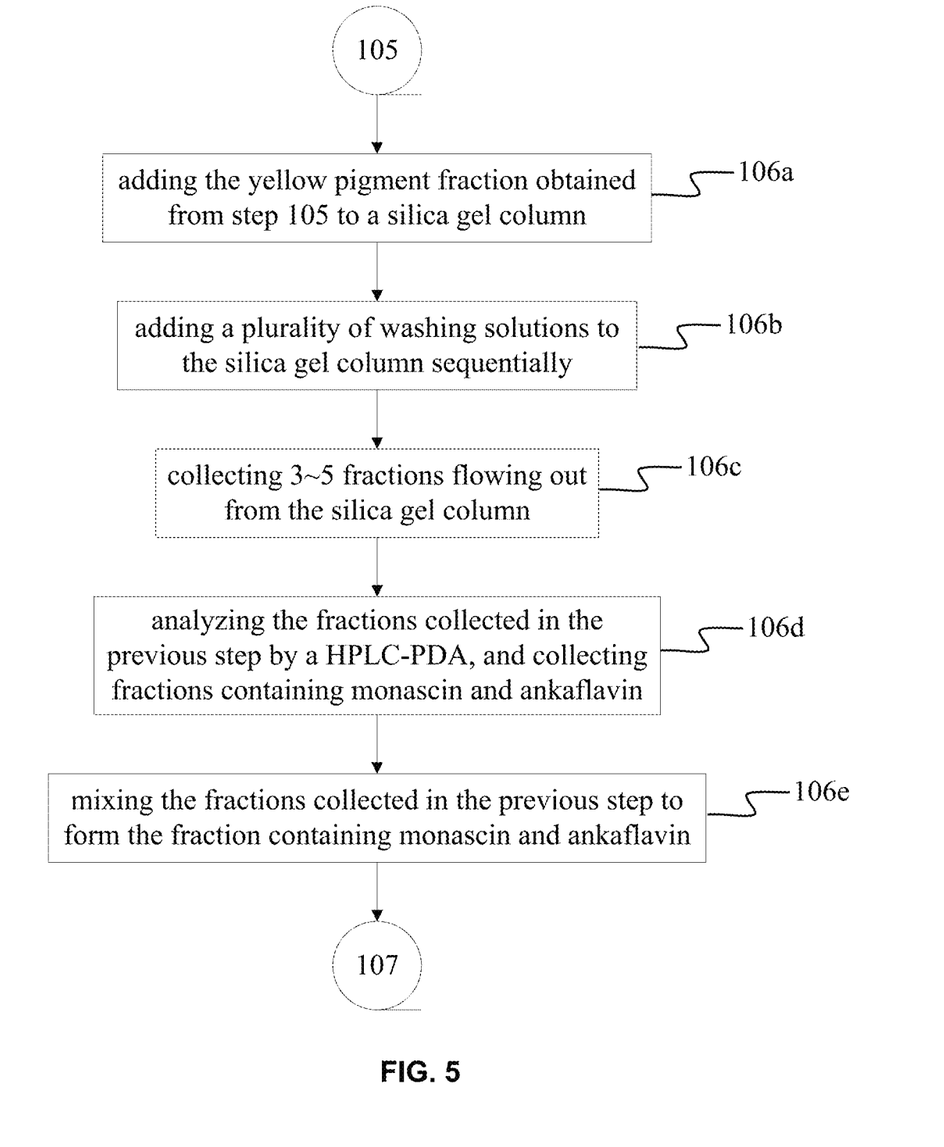
FIG. 5 is a flow chart diagram of detailed steps of step 106 according to the first preferred embodiment of the present invention.

Referring to FIG. 5, which is a flow chart diagram of detailed steps of step 106 according to the first preferred embodiment of the present invention. The above step 106 can be subdivided into the following steps of: (step 106a) adding the yellow pigment fraction obtained from step 105 to a silica gel column; (step 106b) adding a plurality of washing solutions to the silica gel column sequentially, wherein the plurality of washing solutions are Dichloromethane:Ethanol=95:5, Dichloromethane:Ethanol=9:1, and Dichloromethane:Ethanol=4:1 sequentially; (step 106c) collecting 3~5 fractions flowing out from the silica gel column, wherein the time period of each fraction flowing out from the silica gel column is 5~10 min; (step 106d) analyzing the fractions collected in the previous step by a HPLC-PDA, and collecting fractions containing monascin and ankaflavin; and (step 106e) mixing the fractions collected in the previous step to form the fraction containing monascin and ankaflavin.

Figure 6:
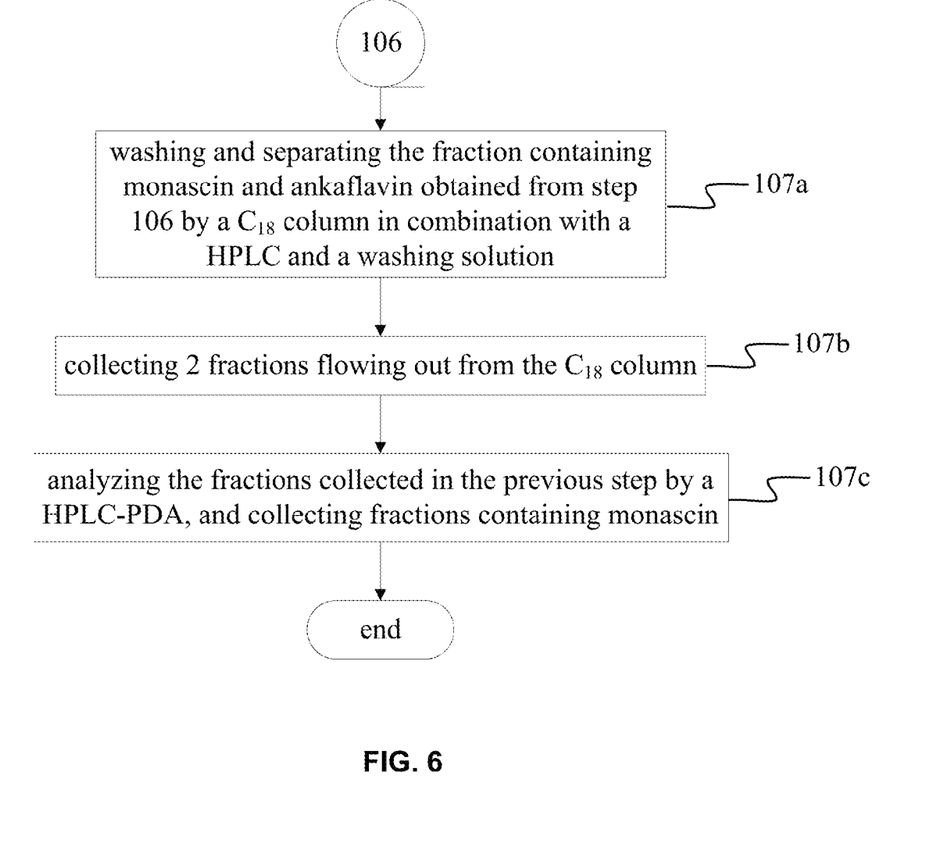
FIG. 6 is a flow chart diagram of detailed steps of step 107 according to the first preferred embodiment of the present invention.

Referring to FIG. 6, which is a flow chart diagram of detailed steps of step 107 according to the first preferred embodiment of the present invention. The above step 107 can be subdivided into the following steps of: (step 107a) washing and separating the fraction containing monascin and ankaflavin obtained from step 106 by a $C_{18}$ column in combination with a HPLC and a washing solution, wherein the washing solution is Methanol:water=85:15; (step 107b) collecting 2 fractions flowing out from the $C_{18}$ column, wherein the time period of each fraction flowing out from the silica gel column is 5~10 min; and (step 107c) analyzing the fractions collected in the previous step by a HPLC-PDA, and collecting fractions containing monascin.

In the above steps 104d, 105d and 106d, the column applied in the HPLC process is C18 column (25 cm*4.6 mm, i.d.=5 μm), the mobile phase is Acetonitrile:water:trifluoroacetate=62:38:0.05, the speed of flow is 1 mL/min, and the UV absorption amount under 231 nm is detected with a multiwavelength detector (because of the curves of monascin and ankaflavin have peaks under 231 nm). Furthermore, standards of monascin and ankaflavin should be applied as comparison groups for comparing the peaks with the ones of analytes, so as to determine whether the analytes are monascin and ankaflavin or not.

Additionally, in the above-mentioned step 107c, the analysis conditions of HPLC process are almost the same as step 104d, step 105d and step 106d. However, the special aspect of step 107c is that monascin and ankaflavin are separated from each other by the property of polarity difference. Owing to the $C_{18}$ column can wash out the more polar ingredients at earlier time point, and monascin is more polar relative to ankaflavin, monascin can be washed out from $C_{18}$ column earlier than ankaflavin. By this property, monascin can be collected in the fractions washed out at earlier time point, and monascin in the fractions can be identified by comparing the washing time and the absorption wavelength with the monascin standard.

Subsequently, the second preferred embodiment of the present invention is described in detail. The composition for lowering blood lipid and elevating high-density lipoprotein according to the second preferred embodiment of the present invention contains ankaflavin, which is a *Monascus* yellow pigment, and extracted from the above-mentioned *Monascus* fermented product. Wherein an amount of the ankaflavin taken by an adult is more than 0.6 mg per day, so that the concentration of blood lipid can be lowered and the concentration of the high-density lipoprotein in blood can be elevated effectively.

Figure 7:
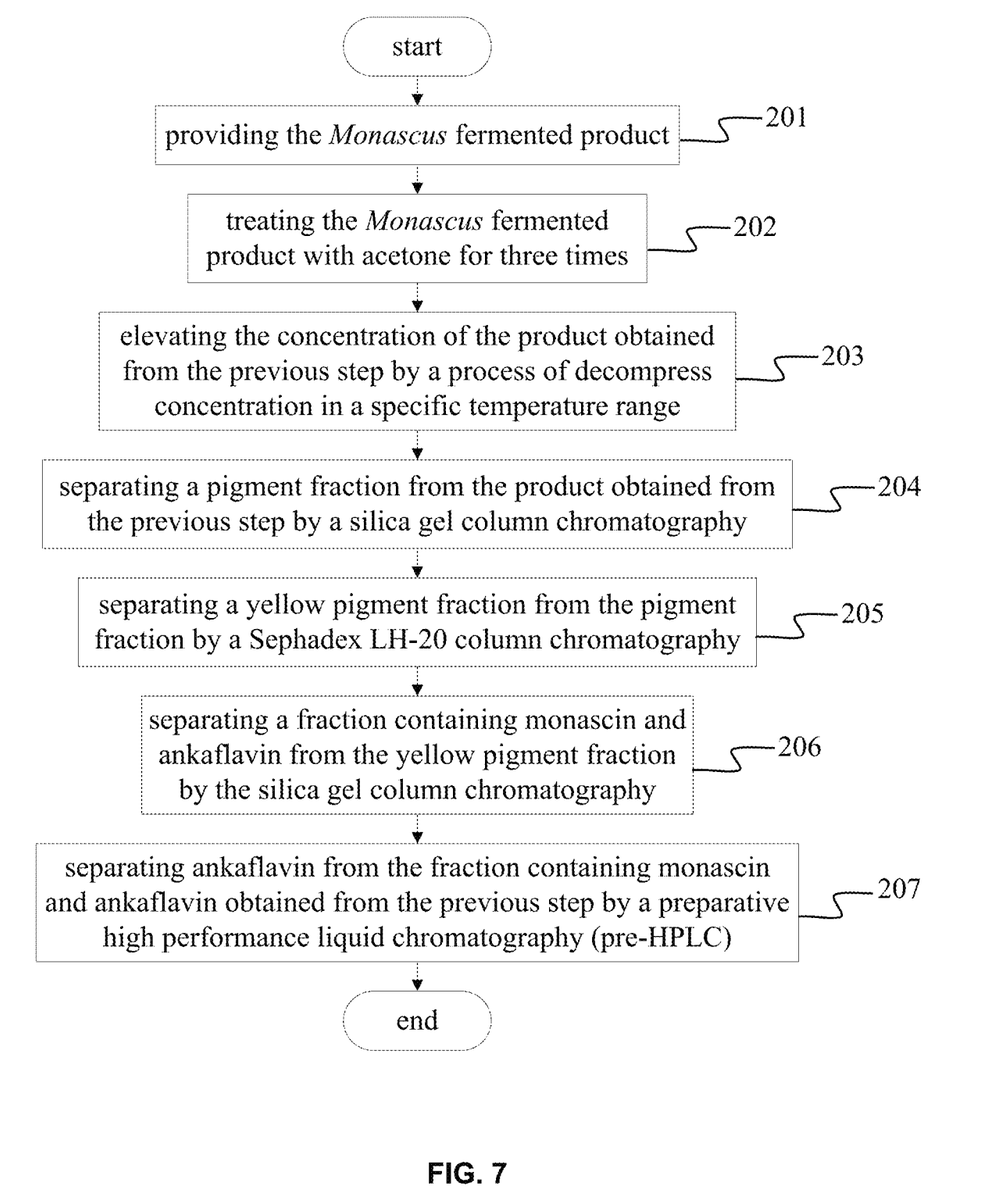
FIG. 7 is a flow chart diagram of a method for manufacturing a composition for lowering blood lipid and elevating high-density lipoprotein according to a second preferred embodiment of the present invention.

Referring to FIG. 7, which is a flow chart diagram of a method for manufacturing the composition for lowering blood lipid and elevating high-density lipoprotein according to the second preferred embodiment of the present invention. Steps 201~206 of the second preferred embodiment are almost the same as the steps 101~106, and thus the steps 201~206 will not be described again here. The difference between the second preferred embodiment and the first preferred embodiment is that step 207 of the second preferred embodiment separates ankaflavin by the pre-HPLC process.

Figure 8:
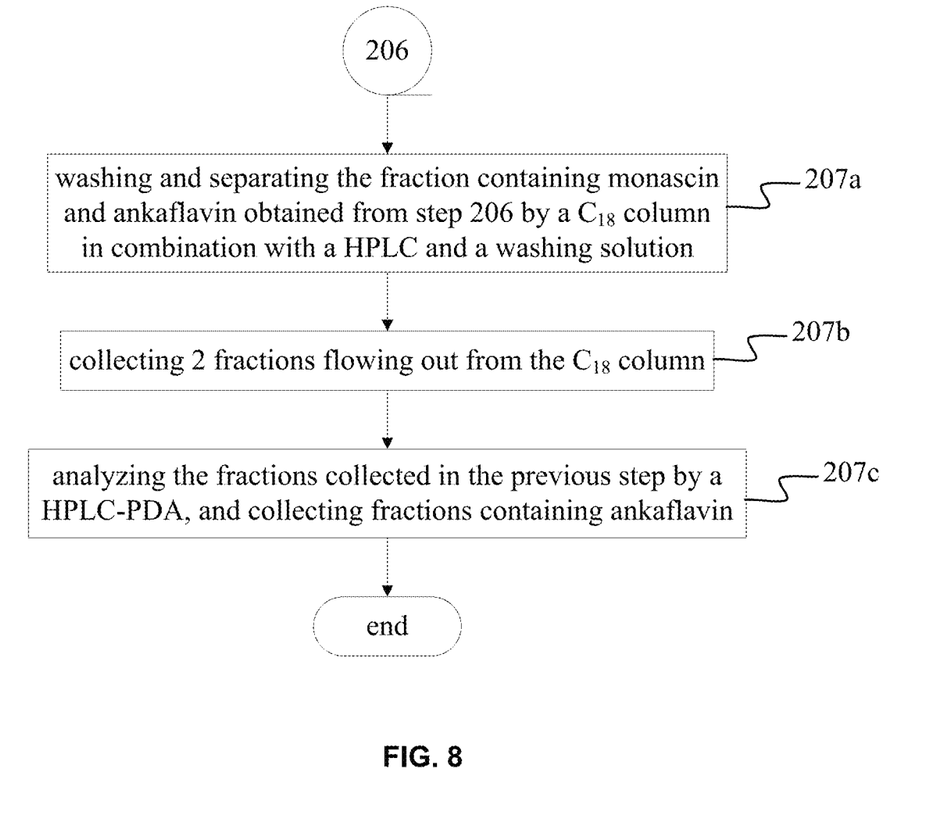
FIG. 8 is a flow chart diagram of detailed steps of step 207 according to the second preferred embodiment of the present invention.

Referring to FIG. 8, which a flow chart diagram of detailed steps of step 207 according to the second preferred embodiment of the present invention. The above step 207 can be subdivided into the following steps of: (step 207a) washing and separating the fraction containing monascin and ankaflavin obtained from step 206 by a $C_{18}$ column in combination with a HPLC and a washing solution, wherein the washing solution in step (7.1) is Methanol:water=85:15; (Step 207b) collecting 2 fractions flowing out from the $C_{18}$ column, wherein the time period of each fraction flowing out from the silica gel column is 5~10 min; and (step 207c) analyzing the fractions collected in the previous step by a HPLC-PDA, and collecting fractions containing ankaflavin.

In the above-mentioned step 207c, monascin and ankaflavin are separated from each other by the property of polarity difference. Owing to the $C_{18}$ column can wash out the more polar ingredients at earlier time point, and monascin is more polar relative to ankaflavin, monascin can be washed out from $C_{18}$ column earlier than ankaflavin. By this property, ankaflavin can be collected in the fractions washed out at later time point, and ankaflavin in the fractions can be identified by comparing the washing time and the absorption wavelength with the ankaflavin standard.

Subsequently, the third preferred embodiment of the present invention is described in detail. The composition for lowering blood lipid and elevating high-density lipoprotein according to the third preferred embodiment of the present invention contains monascin and ankaflavin, which are both *Monascus* yellow pigments, and extracted from the above-mentioned *Monascus* fermented product. Wherein the content ratio of the monascin to the ankaflavin is in a range from 1:1 to 10:1, and the optimum content ratio of the monascin to the ankaflavin is 3.56:1. Furthermore, an amount of the monascin taken by an adult is more than 2.4 mg per day, and an amount of the ankaflavin taken by an adult is more than 0.6 mg per day, so that the concentration of blood lipid can be lowered and the concentration of the high-density lipoprotein in blood can be elevated effectively.

Figure 9:
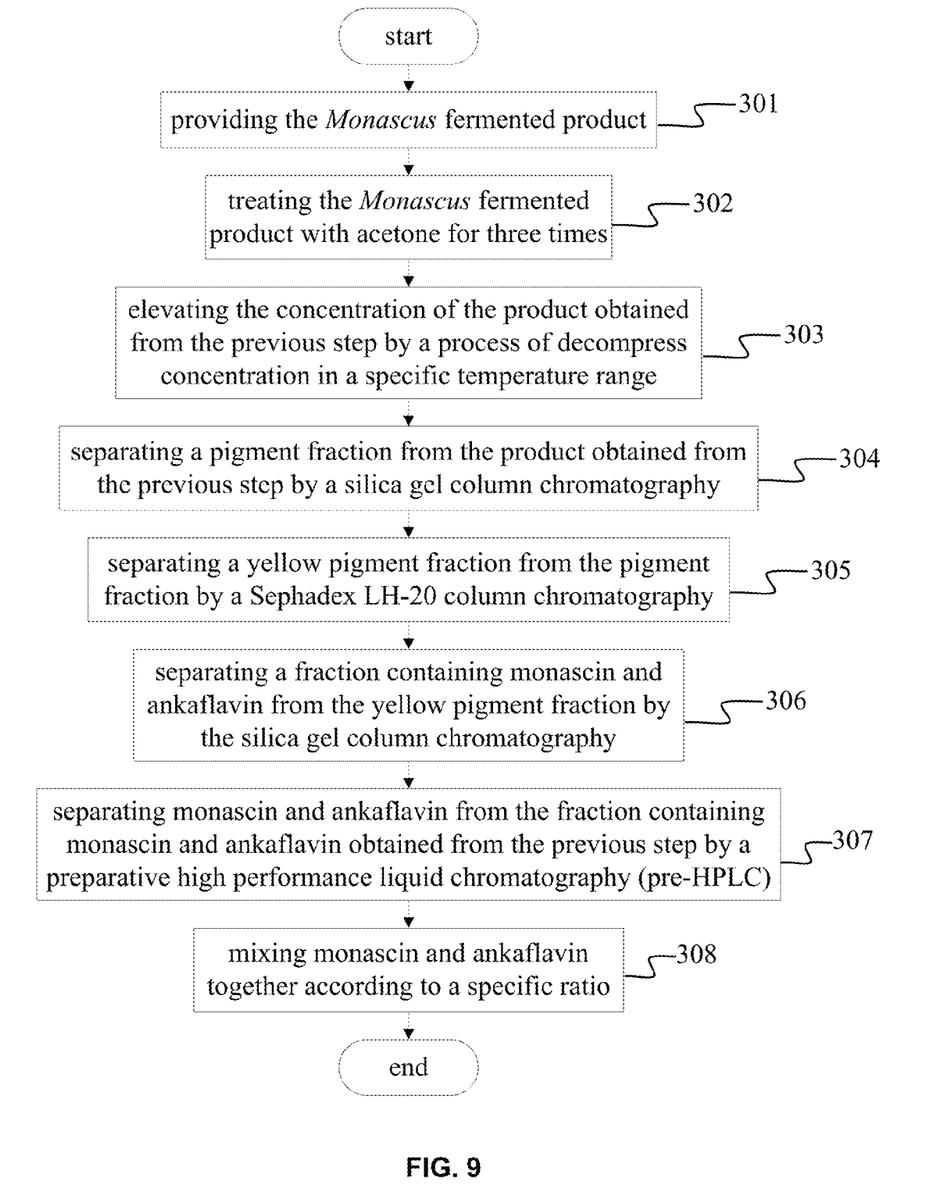
FIG. 9 is a flow chart diagram of a method for manufacturing a composition for lowering blood lipid and elevating high-density lipoprotein according to a third preferred embodiment of the present invention.

Referring to FIG. 9, which is a flow chart diagram of a method for manufacturing the composition for lowering blood lipid and elevating high-density lipoprotein according to the third preferred embodiment of the present invention. Steps 301~306 of the third preferred embodiment are almost the same as the steps 101~106 and 201~206, and thus the steps 301~306 will not be described again here. The difference between the third preferred embodiment and the first preferred embodiment (or second preferred embodiment) is that step 307 of the third preferred embodiment separates monascin and ankaflavin by the pre-HPLC process. Eventually, according to step 308, mixing monascin and ankaflavin together according to a specific ratio, wherein the specific ratio is in a range from 1:1 to 10:1, and the optimum value of the specific ratio is 3.56:1.

Figure 10:
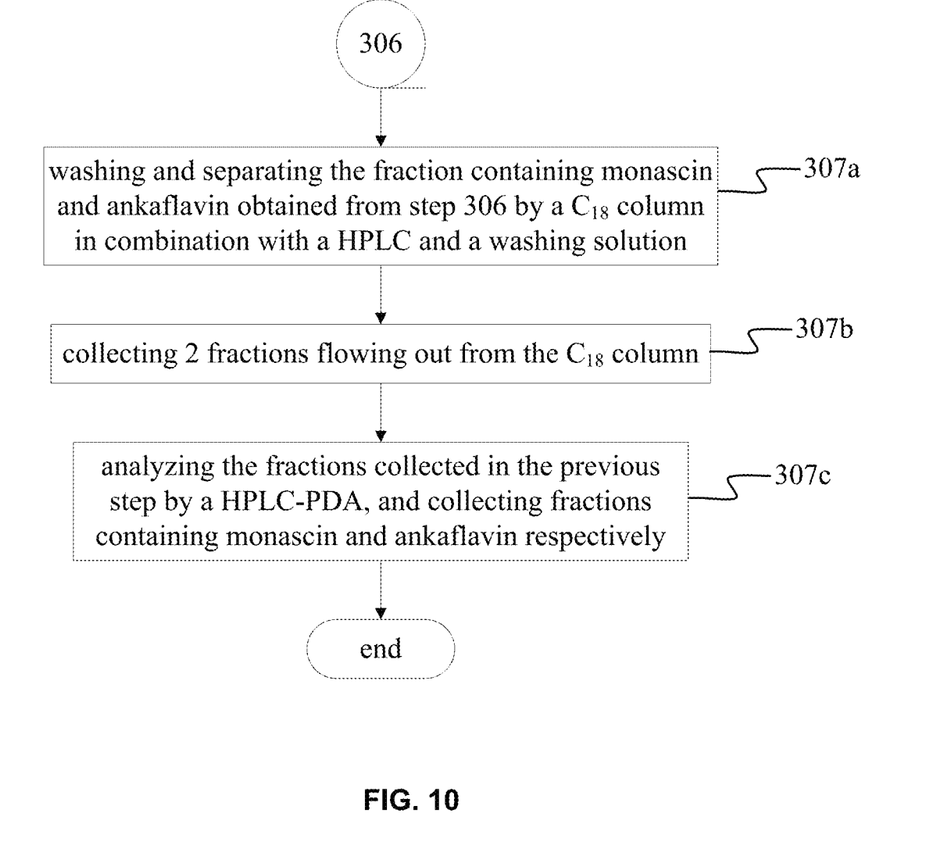
FIG. 10 is a flow chart diagram of detailed steps of step 307 according to the third preferred embodiment of the present invention.

Referring to FIG. 10, which is a flow chart diagram of detailed steps of step 307 according to the third preferred embodiment of the present invention. The above step 307 can be subdivided into the following steps of: (step 307a) washing and separating the fraction containing monascin and ankaflavin obtained from step 306 by a $C_{18}$ column in combination with a HPLC and a washing solution, wherein the washing solution is Methanol:water=85:15; (step 307b) collecting 2 fractions flowing out from the $C_{18}$ column, wherein the time period of each fraction flowing out from the $C_{18}$ column is about 5~10 min; and (step 307c) analyzing the fractions collected in the previous step by a HPLC-PDA, and collecting fractions containing monascin and ankaflavin respectively.

In the above-mentioned step 307c, monascin and ankaflavin are separated from each other by the property of polarity difference. Owing to the $C_{18}$ column can wash out the more polar ingredients at earlier time point, and monascin is more polar relative to ankaflavin, monascin can be washed out from $C_{18}$ column earlier than ankaflavin. By this property, monascin can be collected in the fractions washed out at earlier time point, and ankaflavin can be collected in the fractions washed out at later time point. Furthermore, monascin and ankaflavin in the fractions can be identified by comparing the washing time and the absorption wavelength with the monascin and ankaflavin standards.

In order to prove that the compositions of the first, the second and the third preferred embodiments indeed have the effect of lowering blood lipid and elevating high-density lipoprotein, the compositions are analyzed and compared for their functions by several experiments as followings. Hereinafter, the composition of the first preferred embodiment is called as monascin (MS for abbreviation), and the amount of the monascin taken by an experimental animal is equivalent to 9.82 mg taken by an adult human per day; the composition of the second preferred embodiment is called as ankaflavin (AF for abbreviation), and the amount of the ankaflavin taken by an experimental animal is equivalent to 1.43 mg taken by an adult human per day; the composition of the third preferred embodiment is called as monascin+ankaflavin (MS+AF for abbreviation), and the amount of the monascin and ankaflavin taken by an experimental animal are equivalent to 9.82 mg and 1.43 mg taken by an adult human per day respectively. Additionally, a composition containing monacolin K is utilized as a comparison group, which is called as MK for abbreviation.

Firstly, the experiment utilizes hamsters feed with high cholesterol diet as experimental animals, which are then feed with MS, AF, MS+AF, and MK for 8 weeks, and then each of cholesterol parameters in blood of the hamsters are analyzed. The cholesterol parameters include total cholesterol (TC), triglyceride (TG), high density lipoprotein cholesterol (HDL-C), low density lipoprotein cholesterol (LDL-C), ratio of LDL-C to HDL-C, and malondialdehyde (MDA). The amount of the MK taken by the experimental animals is equivalent to 2.89 mg taken by an adult human per day. Additionally, a normal diet group is referred to as NOR, and a high cholesterol diet group is referred to as HC.

Referring to the following table 1 and table 2, wherein the table 1 illustrates the results of the above-mentioned animal experiments, and the table 2 illustrates the reducing rate or the increasing rate of MS, AF, MS+AF, and MK relative to HC. In the results of the reducing rate of TC, the groups of MS and AF both can lower the amount of TC in serum significantly, and the effect of MS and AF are better than that of MK; the group of MS+AF has the effect of lowering the amount of TC better than the other groups. In the results of the reducing rate of TG, groups of MS, AF and MK+AF can lower the amount of TG in serum significantly, and the effect of MS, AF and MS+AF are better than that of MK. In the results of the increasing rate of HDL-C, the groups of MS and AF both can increase the amount of TC in serum significantly, and the effect of MS and AF are better than that of MK; the group of MS+AF has the effect of increasing the amount of HDL-C better than the other groups. In the results of the reducing rate of LDL-C, although the group of MS has the effect almost the same as MK, the groups of AF and MS+AF have the effect of lowering the amount of LDL-C better than the MK group. In the results of the reducing rate of LDL/HDL, the effect of MS group is better than MK group, and the effects of AF and MS+AF are better than the other groups, thus monascin, ankaflavin and monascin+ankaflavin is more contributive to ameliorate the occurrence of cardiovascular diseases and atherosclerosis than monacolin K. In the results of the reducing rate of MDA, the groups of MS, AF and MS+AF can lower the amount of MDA in serum significantly, and the effects of the groups of MS, AF and MS+AF are all better than the MK group.

TABLE 1

| Group | TC content (mg/dL) | TG content (mg/dL) | HDL-C content (mg/dL) | LDL-C content (mg/dL) | LDL/HDL | MDA content (mg/dL) |
|---|---|---|---|---|---|---|
| NOR | 111.8 ± 10.7 | 168.8 ± 35.6 | 66.6 ± 5.97 | 19.9 ± 2.59 | 0.278 ± 0.038 | 8.93 ± 1.79 |
| HC | 236.5 ± 18.9 | 226.3 ± 76.5 | 98.1 ± 8.89 | 68.3 ± 9.75 | 0.569 ± 0.093 | 11.80 ± 1.85 |
| MK | 190.3 ± 25.1 | 131.1 ± 36.7 | 96.9 ± 8.84 | 45.0 ± 6.97 | 0.489 ± 0.050 | 10.37 ± 1.73 |
| MS | 165.8 ± 10.6 | 82.8 ± 9.0 | 114.2 ± 9.36 | 45.1 ± 3.36 | 0.416 ± 0.022 | 8.62 ± 1.45 |
| AF | 168.9 ± 11.5 | 94.5 ± 18.0 | 118.6 ± 8.09 | 39.4 ± 5.80 | 0.355 ± 0.049 | 9.07 ± 1.45 |
| MS + AF | 160.3 ± 7.6 | 85.6 ± 10.60 | 125.7 ± 7.30 | 38.5 ± 3.10 | 0.351 ± 0.051 | 8.45 ± 1.23 |

TABLE 2

| group | TC reducing rate (%) | TG reducing rate (%) | HDL-C increasing rate (%) | LDL-C reducing rate (%) | LDL/HDL reducing rate (%) | MDA reducing rate (%) |
|---|---|---|---|---|---|---|
| MK | 19.6 | 42.1 | −1.2 | 34.1 | 14.1 | 16.5 |
| MS | 29.9 | 63.4 | 14.1 | 33.9 | 26.9 | 40.1 |
| AF | 28.6 | 58.2 | 17.3 | 42.3 | 37.6 | 59.6 |
| MS + AF | 29.2 | 63.8 | 22.0 | 43.6 | 38.3 | 58.9 |

Figure 11:
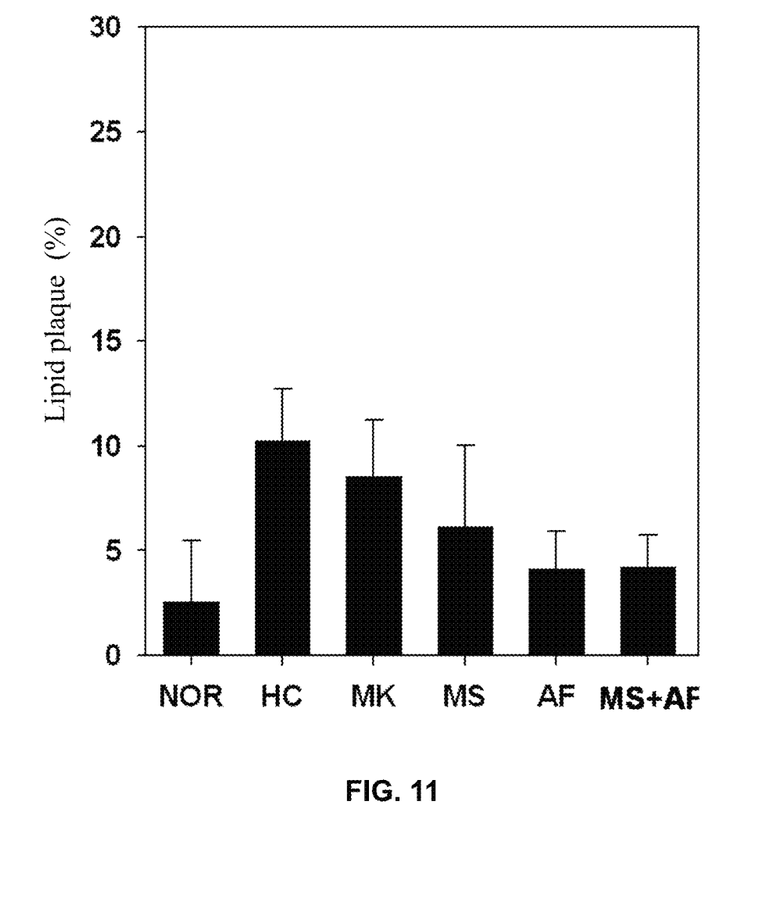
FIG. 11 is a diagram of quantitative results of a lipid plaque staining experiment.

Another important indicator for evaluating atherosclerosis is the analysis of lipid plaque staining in arteries, and the results of lipid plaque staining can indicate that whether lipid plaque deposits on arterial vascular walls. Large amounts of lipid with over-oxidation can cause bulk deposition of foam cells, and then the vascular walls lose elasticity and large amounts of lipid plaque are deposited, so as to lead to atherosclerosis. Referring to FIG. 11, which is a diagram of quantitative results of the lipid plaque staining experiment. The results demonstrate that high cholesterol diet (HC group) for eight weeks may cause the experimental animals to deposit large amounts of lipid plaque on arterial vascular walls in the thoracic cavity, but the deposition of lipid plaque in the NOR group is less than HC group. Although the MK group (the amount of the MK taken is 2.89 mg taken by an adult human per day) can lower the amount of lipid plaque, the effect of the MK group is not as good as that of the MS (the amount of the MS taken is 9.82 mg taken by an adult human per day), AF (the amount of the AF taken is 1.43 mg taken by an adult human per day) and MS+AF groups (the content ratio of the monascin to the ankaflavin is 3.56:1); the effect of the AF group is better than that of the MS group, and the effect of the MS+AF group is better than that of the AF group.

Figure 12:
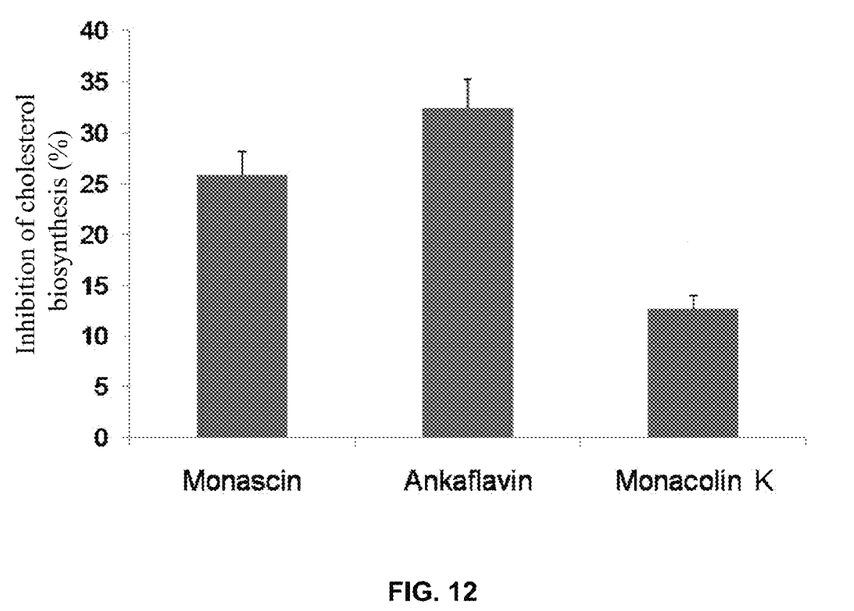
FIG. 12 is a comparative diagram for the effect of the inhibition of cholesterol by monascin, ankaflavin and monacolin K with the same concentration.

In order to compare the inhibitory effect of cholesterol biosynthesis by monascin, ankaflavin and monacolin K, the present invention applies a cell experiment and treats cells with monascin, ankaflavin and monacolin K with the same concentration (100 ppb) for researching the influence of these ingredients on the cholesterol biosynthesis. Referring to FIG. 12, which is a comparative diagram for the effect of the inhibition of cholesterol by monascin, ankaflavin and monacolin K with the same concentration. The results demonstrate that ankaflavin has the best effect of inhibiting the biosynthesis of cholesterol, followed by monascin, and monacolin K has the weakest effect. These results are consistent with the above animal experiments, that is ankaflavin and monascin have better effect on blood lipid lowering than monacolin K.

It can be known from the above experiments that monascin, ankaflavin and monascin+ankaflavin can reduce TC, TG, LDL-C, MDA, and lipid plaque significantly, and can elevate the content of HDL-C in serum; additionally, the effect of monascin+ankaflavin is more prominent than the effect of monascin or ankaflavin. Thus, the compositions according to the first, second and third preferred embodiments not only can reduce the content of cholesterol in serum, but also can elevate the concentration of HDL-C in serum, so as to have extreme contribution to lower the incidence of cardiovascular diseases and atherosclerosis.

By the detailed description of the overall structure and technical content of the present invention, the following advantages of the present invention can be derived:

1. Each of the compositions provided by the present invention all have the effect of lowering blood lipid and elevating high-density lipoprotein, thus these compositions can be utilized to prevent and treat cardiovascular diseases and atherosclerosis.
2. Through the manufacturing method provided by the present invention, each of the compositions with high purity of the present invention can be extracted, and can be applied to lower the incidence of cardiovascular diseases and atherosclerosis.
3. Each of the compositions of the present invention are extracted from *Monascus* fermented product, not synthesized artificially, thus the compositions can be regarded as natural food supplements, which not only can reduce the incidence of cardiovascular diseases and atherosclerosis, but also can avoid the production of side effects.

It should be understood that the embodiments of the present invention described herein are merely illustrative of the technical concepts and features of the present invention and are not meant to limit the scope of the invention. Those skilled in the art, after reading the present disclosure, will know how to practice the invention. Various variations or modifications can be made without departing from the spirit of the invention. All such equivalent variations and modifications are intended to be included within the scope of the invention.

As a result of continued thinking about the invention and modifications, the inventors finally work out the designs of the present invention that has many advantages as described above. The present invention meets the requirements for an invention patent, and the application for a patent is duly filed accordingly. It is expected that the invention could be examined at an early date and granted so as to protect the rights of the inventors.

What is claimed is:

1. A method for manufacturing a composition for lowering blood lipid and elevating high-density lipoprotein, wherein the method comprises the steps of:
   (1) providing a *Monascus* fermented product;
   (2) treating the *Monascus* fermented product with acetone for three times, so as to obtain an extract from the *Monascus* fermented product, wherein the ratio between the *Monascus* fermented product and the acetone is ranged from 1:10 to 1:50;
   (3) enhancing the concentration of the extract obtained from the step (2) by a process of decompress concentration in a specific temperature ranged between 40° C. and 60° C.;
   (4.1) adding the extract obtained from the step (3) into a silica gel column;
   (4.2) adding a plurality of washing solutions into the silica gel column sequentially, wherein the plurality of washing solutions are sequentially hexane, hexane ethanol mixture with the volume ratio of hexane to ethanol being nine to 1 (9:1), hexane ethanol mixture with the volume ratio of hexane to ethanol being eight to two (8:2), hexane ethanol mixture with the volume ratio of hexane to ethanol being seven to three (7:3), hexane ethanol mixture with the volume ratio of hexane to ethanol being five to five (5:5), and ethanol;
   (4.3) collecting 12~15 fractions flowing out from the silica gel column;
   (4.4) analyzing the fractions collected in the step (4.3) by using a high performance liquid chromatography (HPLC) in combination with a photodiode-array (PDA), and then collecting fractions containing monascin and ankaflavin;
   (4.5) mixing the fractions containing the monascin and the ankaflavin collected in the step (4.4), so as to form a pigment fraction;
   (5.1) adding the pigment fraction into a Sephadex LH-20 column;
   (5.2) adding a washing solution into the Sephadex LH-20 column, wherein the washing solution is a methanol acetonitrile mixture with the volume ratio of methanol to acetonitrile being nine to one (9:1);
   (5.3) collecting 3~5 fractions flowing out from the Sephadex LH-20 column;
   (5.4) analyzing the fractions collected in the step (5.3) by using one HPLC-PDA, and further collecting fractions containing monascin and ankaflavin;
   (5.5) mixing the fractions containing the monascin and the ankaflavin collected in the step (5.4) to form a yellow pigment fraction;
   (6.1) adding the yellow pigment fraction obtained from step (5.5) into a silica gel column;
   (6.2) adding a plurality of washing solutions to the silica gel column sequentially, wherein the plurality of washing solutions are sequentially dichloromethane, dichloromethane ethanol mixture with the volume ratio of dichloromethane to ethanol being ninety five to five (95:5), dichloromethane ethanol mixture with the volume ratio of dichloromethane to ethanol being nine to one (9:1), and dichloromethane ethanol mixture with the volume ratio of dichloromethane to ethanol being four to one (4:1);
   (6.3) collecting 3~5 fractions flowing out from the silica gel column;
   (6.4) analyzing the fractions collected in the step (6.3) by using a HPLC in combination with a PDA, and further collecting fractions containing monascin and ankaflavin;
   (6.5) mixing the fractions containing the monascin and the ankaflavin collected in the step (6.3) to form the fraction containing high-purity monascin and high-purity ankaflavin;
   (7.1) washing and separating the fraction containing the high-purity monascin and the high-purity ankaflavin obtained from the step (6.5) by using a C18 column in combination with one HPLC, wherein the washing solution is a methanol water mixture with the volume ratio of methanol to water is eighty five to fifteen (85:15);
   (7.2) collecting 2 fractions flowing out from the C18 column; and
   (7.3) analyzing the fractions collected in the step (7.2) by using a HPLC in combination with a PDA, and then collecting fractions containing the high-purity ankaflavin.

2. The method for manufacturing the composition for lowering blood lipid and elevating high-density lipoprotein according to claim 1, wherein a daily dose composition for an adult comprises an amount of more than 0.6 mg of the ankaflavin extracted from the yellow pigment fraction.

\* \* \* \* \*